United States Patent [19]
Bezwada et al.

[11] Patent Number: 5,633,343
[45] Date of Patent: May 27, 1997

[54] HIGH STRENGTH, FAST ABSORBING, MELT PROCESSABLE, GYCOLIDE-RICH, POLY(GLYCOLIDE-CO-P-DIOXANONE) COPOLYMERS

[75] Inventors: Rao S. Bezwada, Whitehouse Station; Kevin Cooper, Warren; Dennis D. Jamiolkowski, Long Valley; Hugh D. Newman, Jr., Chester, all of N.J.

[73] Assignee: Ethicon, Inc., Somerville, N.J.

[21] Appl. No.: 497,127

[22] Filed: Jun. 30, 1995

[51] Int. Cl.[6] ..................... C08G 63/06
[52] U.S. Cl. ............ 528/361; 525/408; 525/411; 525/413; 525/415; 528/354; 528/357; 606/228; 606/230; 606/231
[58] Field of Search ............... 528/354, 357, 528/361; 525/408, 411, 413, 415; 606/228, 230, 231

[56] References Cited

U.S. PATENT DOCUMENTS

| | | |
|---|---|---|
| 4,838,267 | 6/1989 | Jamiolkowski et al. .......... 128/335.5 |
| 5,076,807 | 12/1991 | Bezwada et al. .......... 606/230 |
| 5,470,340 | 11/1995 | Bezwada et al. .......... 606/231 |

*Primary Examiner*—Terressa Mosley
*Attorney, Agent, or Firm*—Emil Richard Skula

[57] ABSTRACT

Absorbable, segmented copolymers of aliphatic polyesters based on lactone monomers glycolide, and p-dioxanone are described. The segmented copolymers exhibit a broad range of properties, especially high strength and stiffness, and fast absorption rates and breaking strength retention (BSR) profiles, useful in a variety of medical devices. Most importantly, for suture applications where Vicryl®-like polyglcolide-polylactide sutures with excellent tensile properties, but shorter BSR profiles than Vicryl® are needed. The copolymers of the present invention have such properties, making them useful in plastic surgery where faster absorption times would lead to less tissue scarring.

20 Claims, 11 Drawing Sheets

FIG. 1    *PRIOR ART*

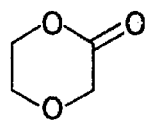

STEP 1. Polymerization of p-dioxanone p-Dioxanone

↓ Catalyst
  Initiator
  100 -130°C

−[OCH$_2$CH$_2$OCH$_2$C(=O)]$_m$  +  residual p-dioxanone monomer

Poly(p-dioxanone) homopolymer

↓ Isolate, dry

−[OCH$_2$CH$_2$OCH$_2$C(=O)]$_m$

Poly(p-dioxanone) homopolymer substantially free of residual p-dioxanone monomer STEP 2. 2nd reactor-Copolymerization of glycolide and poly(p-dioxanone) to form block copolymer

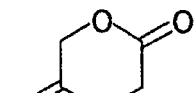  +  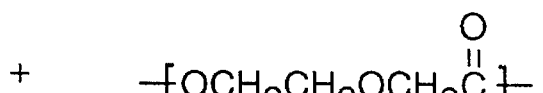

Glycolide        Poly(p-dioxanone) substantially free of p-dioxanone monomer

↓ 140-240°C

−[OCH$_2$C(=O)]$_n$−[OCH$_2$CH$_2$OCH$_2$C(=O)]$_m$

Poly(p-dioxanone-co-glycolide) Block Copolymers

FIG. 2  *PRIOR ART*
STEP 1. Polymerization of p-dioxanone
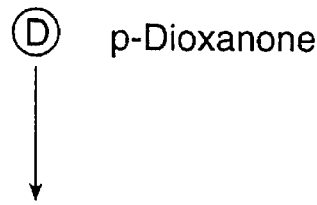
Poly(p-dioxanone) homopolymer "PDO"
STEP 2. Copolymerization of glycolide, and poly(p-dioxanone) homopolymer to form block copolymer
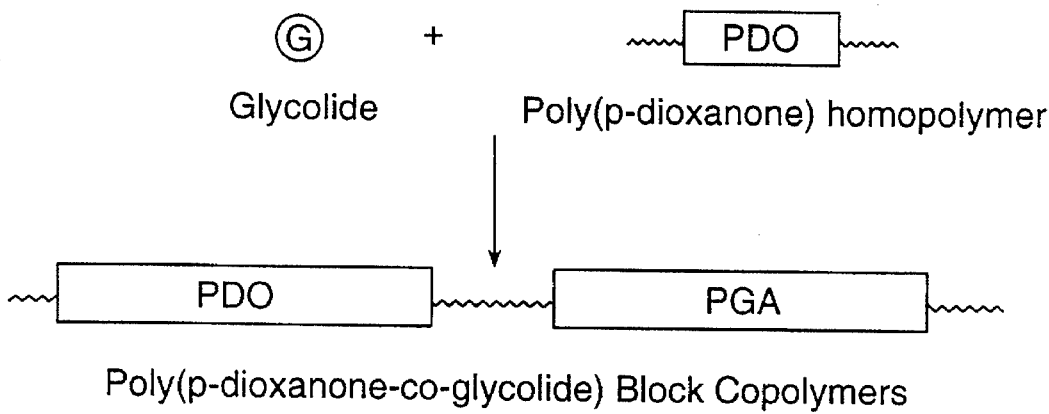
Poly(p-dioxanone-co-glycolide) Block Copolymers

FIG. 3   PRIOR ART
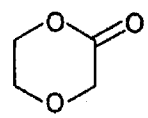
STEP 1. Polymerization of p-dioxanone
p-Dioxanone
↓ Catalyst
Initiator
180°C
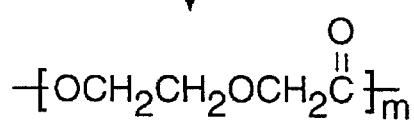
Poly(p-dioxanone) homopolymer
STEP 2. Copolymerization of glycolide,
and poly(p-dioxanone) to form block or graft copolymer
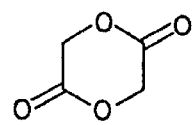 + 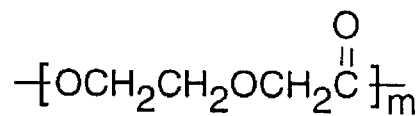
Glycolide          Poly(p-dioxanone)
↓ 200°C
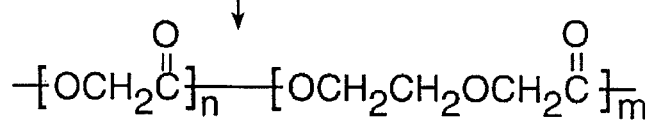
Poly(p-dioxanone-co-glycolide) Block or Graft Copolymers

FIG. 4  *PRIOR ART*
STEP 1. Polymerization of p-dioxanone
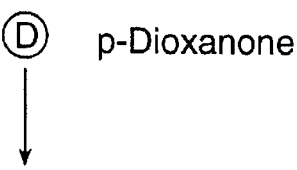
Poly(p-dioxanone) homopolymer "PDO"
STEP 2. Copolymerization of glycolide,
and poly(p-dioxanone)
homopolymer to form block or graft copolymer
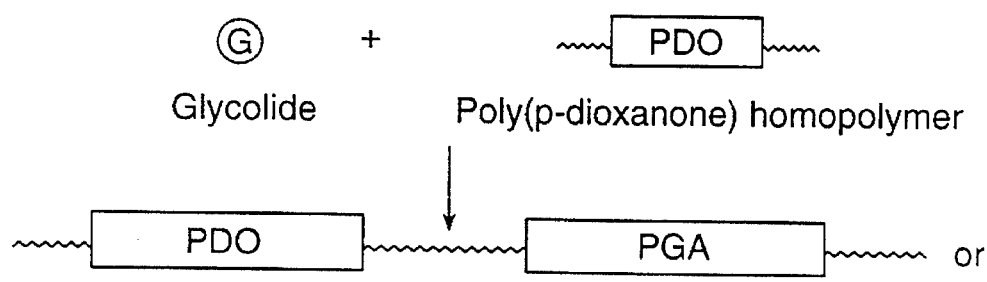
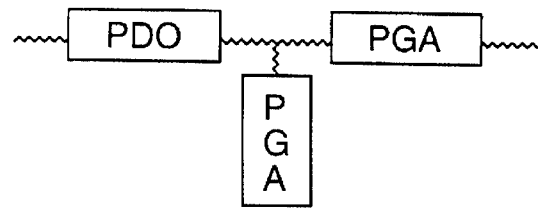
Poly(p-dioxanone-co-glycolide) Block or Graft Copolymers
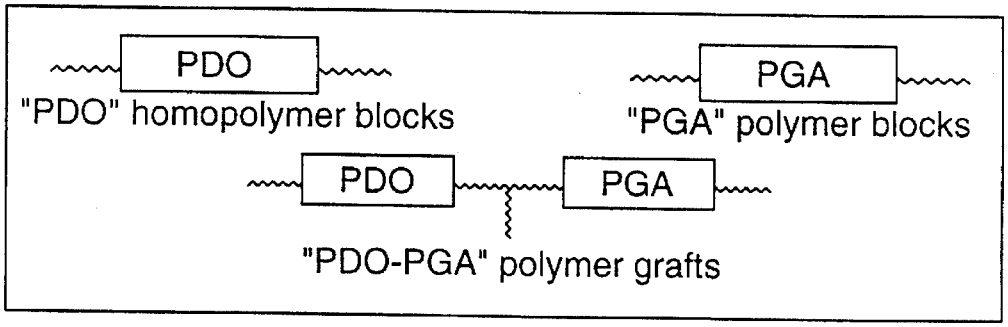

FIG. 5  PRIOR ART

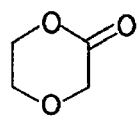 STEP 1. Partial polymerization of p-dioxanone p-Dioxanone  | Catalyst Initiator
100-130°C

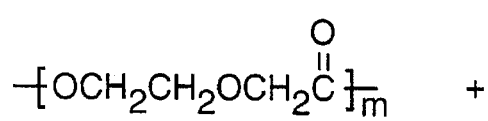 + 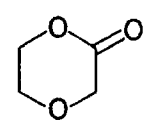

Poly(p-dioxanone) homopolymer "PDO"     p-dioxanone

STEP 2. Copolymerization of glycolide, and poly(p-dioxanone) homopolymer and p-dioxanone monomer to form segmented copolymer

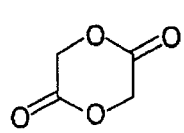 + 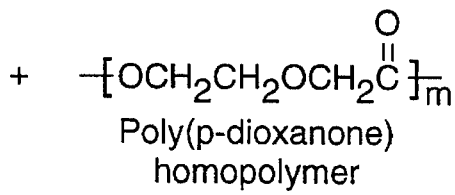 + 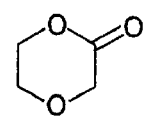

Glycolide     Poly(p-dioxanone) homopolymer     p-dioxanone 120-180° C for glycolide copolymers

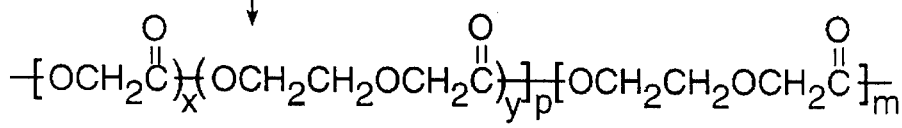

Poly(p-dioxanone-co-glycolide) Segmented Copolymers m>>p, and
"PDO" weight percent
is about 70 to 98%

FIG. 6   *PRIOR ART*

STEP 1. Polymerization of p-dioxanone

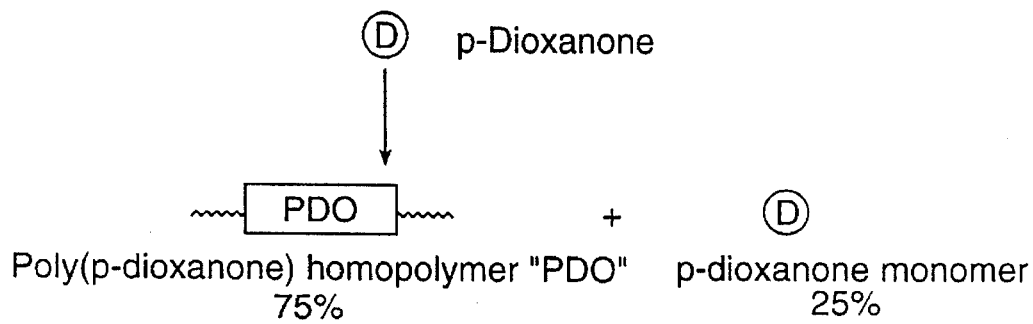

Poly(p-dioxanone) homopolymer "PDO"   p-dioxanone monomer
75%                                    25%

STEP 2. Copolymerization of glycolide, and poly(p-dioxanone) homopolymer and p-dioxanone monomer to form segmented copolymer

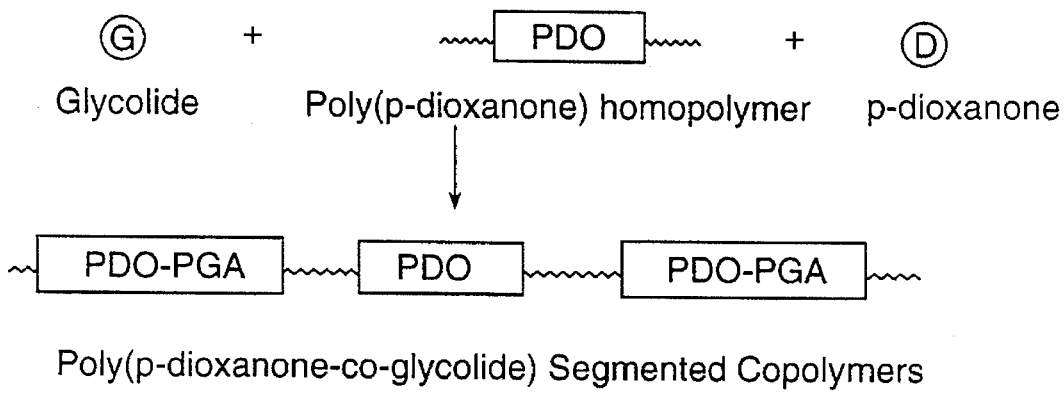

Poly(p-dioxanone-co-glycolide) Segmented Copolymers

"PDO" homopolymer segments

"PDO-PGA" polymer segments

PDO segments >> PDO-PGA segments

FIG. 7

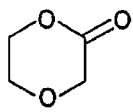

STEP 1. Partial polymerization of p-dioxanone p-Dioxanone

↓ Catalyst Initiator
100-130°C

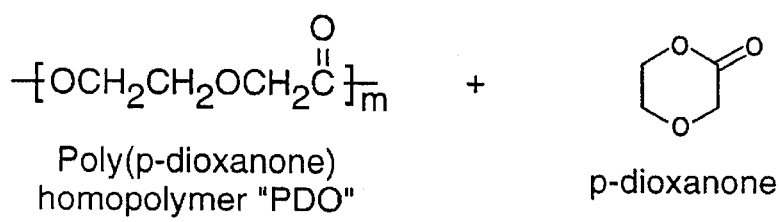

Poly(p-dioxanone) homopolymer "PDO"     p-dioxanone

STEP 2. Copolymerization of glycolide, and poly(p-dioxanone) homopolymer and p-dioxanone monomer to form segmented copolymer

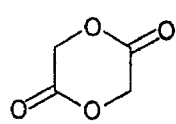 + 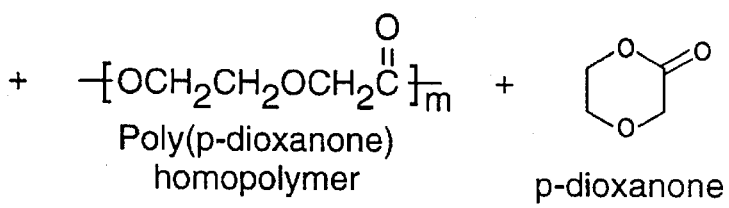 + 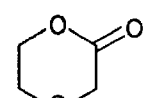

Glycolide     Poly(p-dioxanone) homopolymer     p-dioxanone

↓ 180-220 °C
for glycolide copolymers

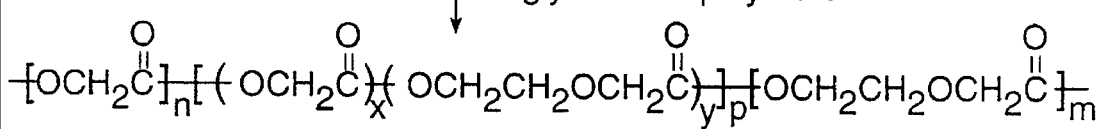

Glycolide-rich, Poly(glycolide-co-p-dioxanone) Segmented Copolymers

FIG. 8
STEP 1. Partial polymerization of p-dioxanone
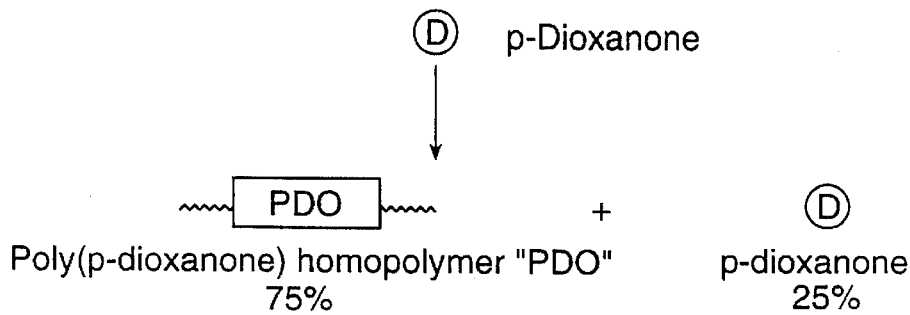
STEP 2. Copolymerization of glycolide, and poly(p-dioxanone) homopolymer and p-dioxanone monomer to form segmented copolymer
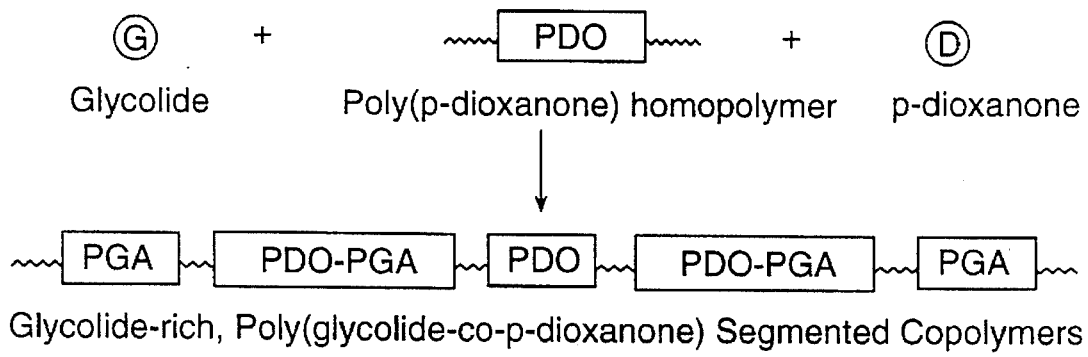
Glycolide-rich, Poly(glycolide-co-p-dioxanone) Segmented Copolymers
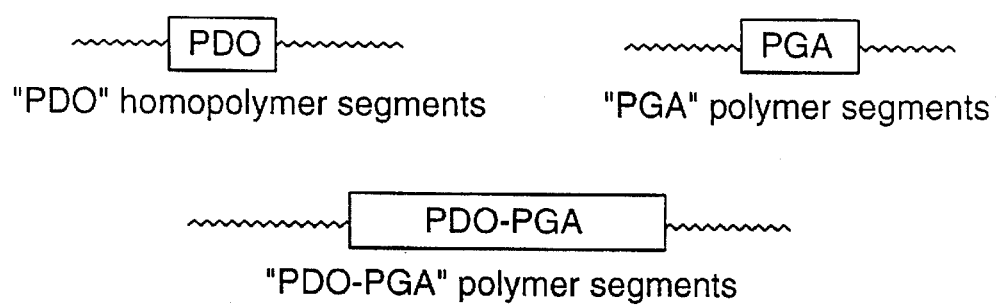

HIGH STRENGTH, FAST ABSORBING, MELT PROCESSABLE, GYCOLIDE-RICH, POLY(GLYCOLIDE-CO-P-DIOXANONE) COPOLYMERS

TECHNICAL FIELD

The field of art to which this invention relates is polymers, more specifically, biocompatible, absorbable copolymers; in particular, segmented copolymers of aliphatic polyesters of glycolide, and p-dioxanone.

BACKGROUND OF THE INVENTION

Polymers, including homopolymers and copolymers, which are both biocompatible and absorbable in vivo are known in the art. Such polymers are typically used to manufacture medical devices which are implanted in body tissue and absorb over time. Examples of medical devices manufactured from these absorbable biocompatible polymers include suture anchor devices, sutures, staples, surgical tacks, clips, plates and screws, etc.

Absorbable, biocompatible polymers useful for manufacturing medical devices include both natural and synthetic polymers. Natural polymers include cat gut, cellulose derivatives, collagen, etc. Synthetic polymers may consist of various aliphatic polyesters, polyanhydrides, poly (orthoester)s, and the like. Natural polymers typically absorb by an enzymatic degradation process in the body, while synthetic absorbable polymers generally degrade primarily by a hydrolytic mechanism.

Synthetic absorbable polymers which are typically used to manufacture medical devices include homopolymers such as poly(glycolide), poly(lactide), poly(e-caprolactone), and poly(p-dioxanone) and copolymers such as poly(lactide-co-glycolide), poly(e-caprolactone-co-glycolide), and poly (glycolide-co-trimethylene carbonate). The polymers may be statistically random copolymers, segmented copolymers, block copolymers, or graft copolymers. It is also known that both homopolymers and copolymers can be used to prepare blends.

U.S. Pat. Nos. 4,653,497, 4,838,267, 5,080,665 describe several biocompatible, absorbable, poly(p-dioxanone-co-glycolide) copolymers useful as biomedical devices. U.S. Pat. Nos. 4,838,267 and 5,080,665 additionally describe poly(p-dioxanone-co-glycolide) block or graft copolymers.

Furthermore, U.S. Pat. No. 4,838,267 describes (See FIGS. 1 and 2) the preparation of poly(p-dioxanone-b-glycolide) block copolymers by a two-step, two-reaction vessel process in which preformed, high molecular weight poly(p-dioxanone), that is substantially free of p-dioxanone monomer, is reacted with glycolide monomer at temperatures from about 140° C. to about 240° C. to yield block copolymers of the (A—B)$_n$ type where A is a long block of repeating units of p-dioxanone (i.e., the homopolymer of poly(p-dioxanone)) and B is a long block of repeating units of glycolide (i.e., the homopolymer of poly(glycolide)). The repeating unit structure as well as a schematic representation of the block copolymer structure are shown in FIGS. 1 and 2. These copolymers are highly crystalline, due to their blocky structure, yielding materials with long breaking strength retention profiles (BSR), high strength and relatively high stiffness. It should be noted that breaking strength retention is a conventionally known standard method of measuring the strength of a device made of a bioabsorbable polymer, as a function of time under biological conditions in vitro or as a function of time after being implanted in vivo.

Additionally, U.S. Pat. No. 5,080,665 describes block or graft copolymers of poly(p-dioxanone-co-glycolide) prepared by a process in which the p-dioxanone monomer is reacted initially for a certain period of time, typically one hour at about 180° C., followed by reaction with glycolide at about 200° C. This process leads to block or graft copolymers which are useful due to their formation of a "hard" phase formed from the glycolide repeating unit blocks, and a "soft" phase formed from the p-dioxanone repeating unit blocks as illustrated in FIGS. 3 and 4.

Furthermore, U.S. Pat. No. 4,653,497 describes poly(p-dioxanone)-rich segmented copolymers comprising about 70 weight percent to about 97 weight percent polymerized p-dioxanone with the remaining small portion of the copolymer polymerized with glycolide as illustrated in FIGS. 5 and 6.

Although the above described copolymers yield materials with excellent properties such as high strength and stiffness and long BSR profiles as found with the block copolymers, or good strength, long elongations, low stiffness and shorter BSR profiles as found for the poly(p-dioxanone)-rich segmented copolymers, there is a need in this art for new copolymer compositions having characteristics of both the block copolymers and the segmented copolymers.

Accordingly, what is needed in this art are novel copolymer compositions which have the block copolymer characteristics of high strength and stiffness, and the segmented copolymer characteristics of shorter BSR profiles and absorptions rates.

In certain biomedical applications there is a strong need for these requirements, including sutures with strong tensile properties, like those of Vicryl® or Dexon®, but shorter BSR profiles and absorption rates.

In addition, it would be highly desirable to have such polymers having little or no unreacted monomers present, since it is believed that the presence of certain levels of unreacted monomers can lead to problems such as adverse tissue reaction.

DISCLOSURE OF THE INVENTION

Surprisingly, it has been discovered that by preparing copolymers of poly(glycolide-co-p-dioxanone) rich in glycolide by a process in which a small proportion of p-dioxanone monomer is reacted at low temperatures from about 100° C. to about 130° C. followed by reaction with glycolide at higher temperatures of about 180° C. to about 220° C., segmented glycolide-rich copolymers with small proportions of p-dioxanone can be formed that have high strength and stiffness, but short BSR profiles and fast absorption rates, making them useful in a variety of biomedical devices such as suture anchor devices, staples, surgical tacks, clips, plates and screws. The copolymers of the present invention are especially useful for suture applications where Vicryl®-like sutures with excellent tensile properties but shorter BSR profiles than Vicryl®are needed. The copolymers of the present invention are, therefore, useful in plastic surgical applications, where faster absorption times tend to result in less tissue scarring. That is, for example, an absorbable suture which rapidly loses strength in the sections which have been implanted beneath a patient's skin can be more easily removed, by use of antitension skin tape, without the pain, discomfort and scarring typically suffered by patients who have had conventional sutures implanted.

Accordingly, novel, absorbable, biocompatible, poly (glycolide-co-p-dioxanone) segmented copolymers are disclosed. The copolymers have a major component comprising about 30 mole percent to about 95 mole percent of repeating units of glycolide, and a minor component comprising about 70 mole percent to about 5 mole percent of repeating units of p-dioxanone.

Yet another aspect of the present invention is a biomedical device made from the above described copolymers, especially implantable devices such as suture anchor devices, staples, surgical tacks, clips, plates and screws, and most especially for suture applications where Vicryl® or Dexon®-like sutures with excellent tensile properties, but shorter BSR profiles than Vicryl® or Dexon® are needed for plastic surgery.

An additional aspect of the present invention is a process for producing the segmented copolymers of the present invention. The initial step of the process is to polymerize p-dioxanone in the presence of a catalytically effective amount of catalyst and an initiator at a sufficient temperature and for a sufficient period of time to effectively yield a first mixture of p-dioxanone monomer and p-dioxanone homopolymer. Then, glycolide is added to the first mixture to form a second mixture. Next, the second mixture is polymerized at a sufficient temperature and for a sufficient amount of time to effectively produce a segmented copolymer comprising a major component comprising about 30 mole percent to about 95 mole percent of repeating units of glycolide and a minor component comprising about 70 mole percent to about 5 mole percent of repeating units of p-dioxanone.

Still yet a further aspect of the present invention is the copolymer of the present invention which is a product of the process of the present invention.

The foregoing and other features and advantages of the invention will become more apparent from the following description and accompanying examples.

BRIEF DESCRIPTION OF THE DRAWINGS

FIG. 1 illustrates a synthetic process for the preparation of poly(p-dioxanone-b-glycolide) block copolymers as described in U.S. Pat. No. 4,838,267.

FIG. 2 illustrates a schematic representation of poly(p-dioxanone-b-glycolide) block copolymers as described in U.S. Pat. 4,838,267.

FIG. 3 illustrates a synthetic process for the preparation of poly(p-dioxanone-co-glycolide) block or graft copolymers as described in U.S. Pat. No. 5,080,665.

FIG. 4 illustrates a schematic representation of poly(p-dioxanone-co-glycolide) block or graft copolymers as described in U.S. Pat. No. 5,080,665.

FIG. 5 illustrates a synthetic process for the preparation of poly(p-dioxanone)-rich, poly(p-dioxanone-co-glycolide) segmented copolymers as described in U.S. Pat. No. 4,653,497.

FIG. 6 illustrates a schematic representation of poly(p-dioxanone)-rich, poly(p-dioxanone-co-glycolide) segmented copolymers as described in U.S. Pat. No. 4,653,497.

FIG. 7 illustrates a synthetic process for the preparation of the glycolide-rich, poly(glycolide-co-p-dioxanone) segmented copolymers of the present invention.

FIG. 8 illustrates a schematic representation of the glycolide-rich, poly(glycolide-co-p-dioxanone) segmented copolymers of the present invention.

DESCRIPTION OF THE PREFERRED EMBODIMENTS

Figure 9:
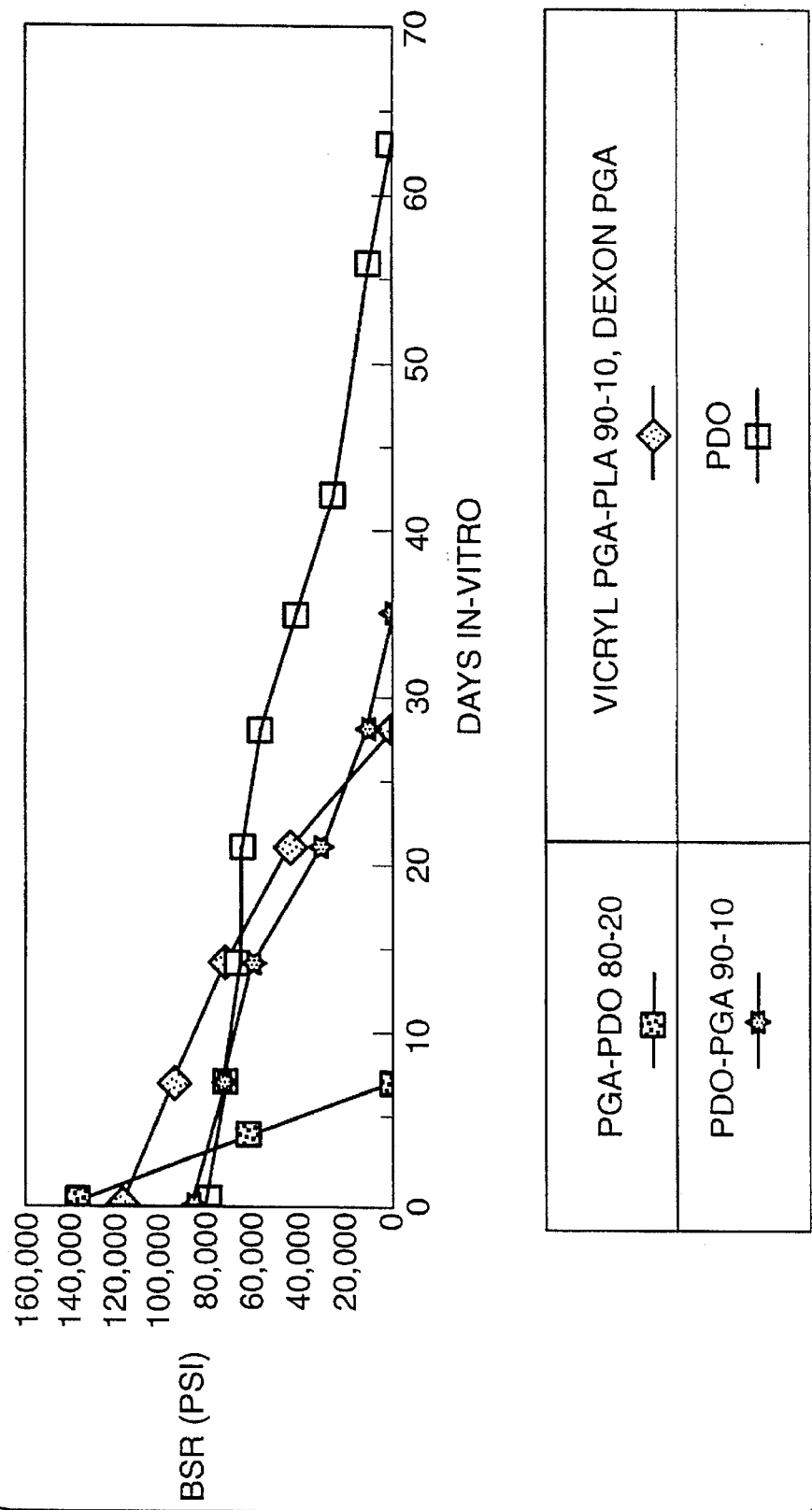
FIG. 9 is a graph presenting BSR profiles of size 4-0 fibers (sutures) of Vicryl (90:10 (mol/mol) poly(glycolide-co-lactide)) or Dexon (poly(glycolide)), size 4-0 fibers of poly(p-dioxanone), size 5-0 fibers of a segmented copolymer of U.S. Pat. No. 4,653,497, and size 5-0 fibers of a 80:20 (mol/mol) segmented poly(glycolide-co-p-dioxanone) copolymer of the present invention.

The process of the present invention is a one-step, one-reaction vessel, two-temperature process in which a mixture of p-dioxanone monomer and p-dioxanone homopolymer is initially formed at low temperatures of from about 100° C. to about 130° C., preferably 110° C. The mixture is then reacted with glycolide at temperatures from about 120° C. to about 220° C. to form copolymers in which segments or sequences are composed of both p-dioxanone and glycolate moieties as illustrated in FIGS. 7 and 8. These segmented copolymers are substantially less crystalline than the block or graft copolymers of the prior art and, therefore, yield materials with good strength, but shorter BSR profiles, faster absorption rates, longer elongations and lower stiffness.

More specifically, the poly(glycolide-co-p-dioxanone) segmented copolymers of the present invention are prepared by a process in which p-dioxanone monomer is reacted in a conventional reactor vessel at low temperatures from about 100° C. to about 130° C., preferably about 110° C., for a sufficient time effective to cause polymerization, preferably about 4 hours to about 8 hours, followed by reaction with glycolide at higher temperatures of about 180° C. to about 220° C. for a sufficient time effective to cause copolymerization, preferably about 1 hour to about 4 hours.

Furthermore, the segmented poly(glycolide-co-p-dioxanone) copolymers will typically consist of about 30 mole percent to about 95 mole percent of glycolate moieties, more preferably about 30 mole percent to about 90 mole percent of glycolate moieties, and most preferably about 30 mole percent to about 50 mole percent of glycolate moieties.

The aliphatic segmented copolyesters useful in the preparation of the segmented copolymers of the present invention will typically be synthesized in a ring opening polymerization. That is, the aliphatic lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

Suitable lactone monomers may be selected from the group consisting of glycolide, lactide (l, d, dl, meso), p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one and combinations of two or more thereof. Preferred lactone monomers are selected from the group consisting of glycolide, and p-dioxanone.

More specifically, the segmented copolymers of poly (glycolide-co-p-dioxanone) useful in the practice of the present invention will typically be synthesized by a process in which p-dioxanone is polymerized in a ring opening polymerization in the presence of an organometallic catalyst and an initiator at elevated temperatures. The organometallic catalyst is preferably tin based, e.g., stannous octoate, and is present in the mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1.

The polymerization is typically carried out in a conventional reactor vessel at a temperature range from about 100° C. to about 130° C., preferably 110° C., for about 4 hours to about 8 hours, preferably about 5 hours to about 6 hours, yielding a mixture of p-dioxanone monomer and homopolymer. Then, glycolide monomer is added to the mixture of p-dioxanone monomer and homopolymer and the temperature is raised to about 180° C. to about 220° C., preferably from about 190° C. to about 220° C. until the desired molecular weight and viscosity are achieved. It should be understood that pure monomers and dry conditions are utilized to achieve such molecular weights.

Under the above described conditions, the segmented copolymers of poly(glycolide-co-p-dioxanone), will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.5 to about 4.0 deciliters per gram (dL/g), more typically 0.7 to about 3.5 dL/g, and most preferably 1.0 to about 3.0 dL/g as measured in a 0.1 g/dL solution of hexafluoroisopropanol (HFIP) at 25° C. Also, it should be noted that under the above described conditions, the residual monomer content will be less than about 5 wt. %.

The segmented copolymers of poly(glycolide-co-p-dioxanone) will typically consists of about 30 mole percent to about 95 mole percent, more preferably about 30 mole percent to about 90 mole percent of glycolate moieties, and most preferably about 30 mole percent to about 50 mole percent of glycolate moieties. The lower limit of glycolate moieties in the copolymers is desirable because the addition of 30 mole percent leads to copolymers which have longer BSR profiles, but lower strength. The upper limit of glycolate moieties in the copolymers is desirable because the addition of 95 mole percent leads to copolymers which have shorter BSR profiles, but higher strength and stiffness. This leads to copolymers with a desirable range of strength, stiffness and absorption profiles for use in a variety of biomedical applications. One skilled in the art will appreciate that the number of moles of glycolate moieties and p-dioxanone moieties in the copolymer are equivalent to the number of moles of glycolide and p-dioxanone monomers needed to be added to the reaction to form the copolymer.

Articles such as medical devices are molded from the segmented copolymers of the present invention by use of various conventional injection and extrusion molding equipment at temperatures ranging from about 160° C. to about 220° C., more preferably 180° C. to about 220° C., with residence times of about 2 to about 10 minutes, more preferably about 2 to about 5 minutes.

The segmented copolymers of the present invention can be melt processed by numerous methods to prepare a vast array of useful devices. These materials can be injection or compression molded to make implantable medical and surgical devices, including wound closure devices. The preferred devices are suture anchor devices, staples, surgical tacks, clips, plates and screws.

Copolymers of the present invention with low levels of p-dioxanone have particular utility in the preparation of absorbable surgical devices that must be stiff and simultaneously tough. Of particular utility are those compositions having p-dioxanone at about 5 to about 30 mole percent.

Alternatively, the segmented copolymers can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or non-woven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed. Especially, sutures with Vicryl®-like tensile properties but shorter BSR profiles than Vicryl® are needed, useful in plastic surgical applications where faster absorption times would lead to less tissue scarring. That is, a suture which rapidly loses strength in the portion which is implanted beneath the skin can be more easily removed, by use of antitension skin tape, without the pain, discomfort and scarring typically suffered by patients who have had conventional sutures implanted. Vicryl® is a trademark for sutres made from polyglycolide-polylactide (90-10) copolymers.

Additionally, the segmented copolymers of the present invention can be molded to form films which, when sterilized, could be useful as adhesion prevention barriers. Another alternative processing technique for the copolymers of the present invention includes solvent casting, particularly for those applications where a drug delivery matrix is desired.

Furthermore, the segmented copolymers of the present invention can be processed by conventional techniques to form foams, which are useful as hemostatic barriers and bone substitutes.

In more detail, the surgical and medical uses of the filaments, films, foams and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. orthopedic pins, clamps, screws, and plates
k. clips
l. staples
m. hooks, buttons, and snaps
n. bone substitutes
o. needles
p. intrauterine devices
q. draining or testing tubes or capillaries
r. surgical instruments
s. vascular implants or supports
t. vertebral discs
u. extracorporeal tubing for kidney and heart-lung machines
v. artificial skin and others
w. stents x. suture anchors
y. injectable defect fillers
z. preformed defect fillers
a1. tissue adhesives and sealants
b2. bone waxes
b3. cartilage replacements
d4. hemostatic barriers

EXAMPLES

The following examples are illustrative of the principles and practice of this invention, although not limited thereto. Numerous additional embodiments within the scope and spirit of the invention will become apparent to those skilled in the art. The examples describe new segmented copolymers of poly(glycolide-co-p-dioxanone), said copolymers being useful as biomedical devices.

In the synthetic process, the high molecular weight aliphatic segmented copolyesters are prepared by a method consisting of reacting p-dioxanone via a ring opening polymerization in a conventional reactor vessel at temperatures of about 100° C. to about 130° C. for about 4 hours to about 8 hours under an inert nitrogen atmosphere, followed by reaction with glycolide at temperatures of 180° C. to 220° C. until the desired molecular weight and viscosity are achieved.

In the examples which follow, the segmented copolymers and monomers were characterized for chemical composition and purity (NMR, FT-IR), thermal analysis (DSC), melt rheology (melt stability and viscosity), and molecular weight (inherent viscosity), and baseline and in vitro mechanical properties (Instron stress/strain).

$^1$H was performed on a 300 MHz NMR using $CDCl_3$ or HFAD as a reference. Thermal analysis of segmented copolymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the segmented copolymers was also determined by a Rheometrics Dynamic Analyzer RDA II for a period of 1 hour at temperatures ranging from 160° C. to 230° C. under a nitrogen atmosphere. Inherent viscosities (I.V., dL/g) of the segmented copolymers were measured using a 50 bore Cannon-Ubbelhode dilution viscometer immersed in a thermostatically controlled water bath at 25° C. utilizing chloroform or hexafluoroisopropanol (HFIP) as the solvent at a concentration of 0.1 g/dL.

Melt viscosity was determined utilizing a Rheometrics Dynamic Analyzer RDA II at temperatures ranging from 160° C. to 230° C. at rate of 1° C./min. to 10° C./min. at frequencies of $1s^{-1}$ to $100s^{-1}$ under a nitrogen atmosphere.

Fibers of copolymers of the present invention were prepared by a method as described in U.S. Pat. No. 4,643,191, which is incorporated herein by reference. The copolymers were melt extruded in a conventional manner using an INSTRON® capillary rheometer or single screw extruder. Rheometer packing temperatures ranged from about 100° C. to about 200° C. with dwell times of about 5 to about 15 minutes and ram speeds of about 1 to about 3 cm/min. Extrusion temperatures ranged from about 160° C. to about 230° C.

The extrudate was typically drawn at a draw rate of 4 feet per minute in a single or mulitstage drawing process with drawing temperatures of about 25° C. to about 75° C., giving a final draw ratio of about 4× to about 8×.

Fibers were also annealed under similar conditions as described in U.S. Pat. No. 4,643,191. Annealing temperatures were from about 70° C. to about 140° C., preferably 110° C., with annealing times of about 1 hour to about 10 hours, preferably about 4 to 7 hours.

In vitro studies were determined in a phosphate buffer solution (pH=7.27) at a temperature of 37° C. for periods of 4, 7, 14, 21, and 28 days. Cylindrical dumbbells (8 to 10 of a total weight of 2.4 to 3.0 grams) or fibers (8 to 10, 6 to 12 inches long) were placed in 100 ml of buffer solution.

Several synthesis examples will be described in the following few pages. Parts and percentages where used are parts and percentages as specified as weight or moles.

EXAMPLE 1

Synthesis of a 80:20 (mol/mol) poly(glycolide-co-p-dioxanone) segmented copolymer To a flame dried 250 ml 2-neck round bottom flask equipped with an overhead mechanical stirrer, nitrogen inlet and glass stopper, 20.42 grams (0.20 moles) of p-dioxanone, 0.057 ml of diethylene glycol as an initiator, and 50.5 microliters of a 0.33M solution of stannous octoate (in toluene) catalyst were added.

The assembly was then placed in a high temperature oil bath at 110° C. The stirred p-dioxanone quickly began to melt. The low viscosity melt quickly increased in viscosity. Stirring of the high viscosity melt was continued for about 6 hours.

Then, 92.90 grams (0.80 moles) of glycolide was added in three equal portions while the temperature was raised gradually to 210° C. The glycolide quickly began to melt and the reaction mass slowly began to increase in viscosity. Stirring of the high viscosity melt was continued for another 0.5 hours for a total reaction time of 2 hours at 210° C. under nitrogen.

The 80:20 (mol/mol) poly(glycolide-co-p-dioxanone) segmented copolymer was removed from the bath, cooled to room temperature under a stream of nitrogen, isolated and ground. The polymer was then dried under vacuum at 80° C. for about 64 hours. The copolymer conversion was about 96.8%. The inherent viscosity was 1.76 dL/g as measured in a 0.1 g/dL HFIP solution at 25° C. The molar ratio of poly(glycolide) to poly(p-dioxanone) was found to be 83.2 to 16.8 by $^1$H NMR.

EXAMPLE 2

Synthesis of a 70:30 (mol/mol) poly(glycolide-co-p-dioxanone) segmented copolymer To a flame dried 250 ml 2-neck round bottom flask equipped with an overhead mechanical stirrer, nitrogen inlet and glass stopper, 30.60 grams (0.30 moles) of p-dioxanone, 0.057 ml of diethylene glycol as an initiator, and 50.5 microliters of a 0.33M solution of stannous octoate (in toluene) catalyst were added.

The assembly was then placed in a high temperature oil bath at 110° C. The stirred p-dioxanone quickly began to melt. The low viscosity melt quickly increased in viscosity. Stirring of the high viscosity melt was continued for about 6 hours.

Then, 81.30 grams (0.70 moles) of glycolide was added in three equal portions while the temperature was raised gradually to 210° C. The glycolide quickly began to melt and the reaction mass slowly began to increase in viscosity. Stirring of the high viscosity melt was continued for another 0.5 hours for a total reaction time of about 2 hours at 210° C. under nitrogen.

The 70:30 (mol/mol) poly(glycolide-co-p-dioxanone) segmented copolymer was removed from the bath, cooled to room temperature under a stream of nitrogen, isolated and ground. The polymer was then dried under vacuum at 80° C.

for about 64 hours. The copolymer conversion was about 95.4%. The inherent viscosity was 2.25 dL/g as measured in a 0.1 g/dL HFIP solution at 25° C. The molar ratio of poly(glycolide) to poly(p-dioxanone) was found to be 75.2 to 24.8 by $^1$H NMR.

EXAMPLE 3

Synthesis of a 60:40 (mol/mol) poly(glycolide-co-p-dioxanone) segmented copolymer To a flame dried 250 ml 2-neck round bottom flask equipped with an overhead mechanical stirrer, nitrogen inlet and glass stopper, 40.84 grams (0.40 moles) of p-dioxanone, 0.057 ml of diethylene glycol as an initiator, and 50.5 microliters of a 0.33M solution of stannous octoate (in toluene) catalyst were added.

The assembly was then placed in a high temperature oil bath at 110° C. The stirred p-dioxanone quickly began to melt. The low viscosity melt quickly increased in viscosity. Stirring of the high viscosity melt was continued for about 6 hours.

Then, 69.64 grams (0.60 moles) of glycolide was added in three equal portions while the temperature was raised gradually to 210° C. The glycolide quickly began to melt and the reaction mass slowly began to increase in viscosity. Stirring of the high viscosity melt was continued for another 0.5 hours for a total reaction time of about 2 hours at 210° C. under nitrogen.

the homopolymers (i.e., the homopolymers of poly(p-dioxanone), or poly(glycolide)) are connected or linked at a single point. Segmented copolymers, as shown in FIGS. 5, 6, 7, and 8, are copolymers where short segments of repeating units composed of both monomeric units are connected or linked at many points.

The differences in the arrangement or sequences of the repeating units in the copolymer can lead to dramatic changes in the thermal, chemical, physical, and for absorbable polymers, biological properties.

Figure 10:
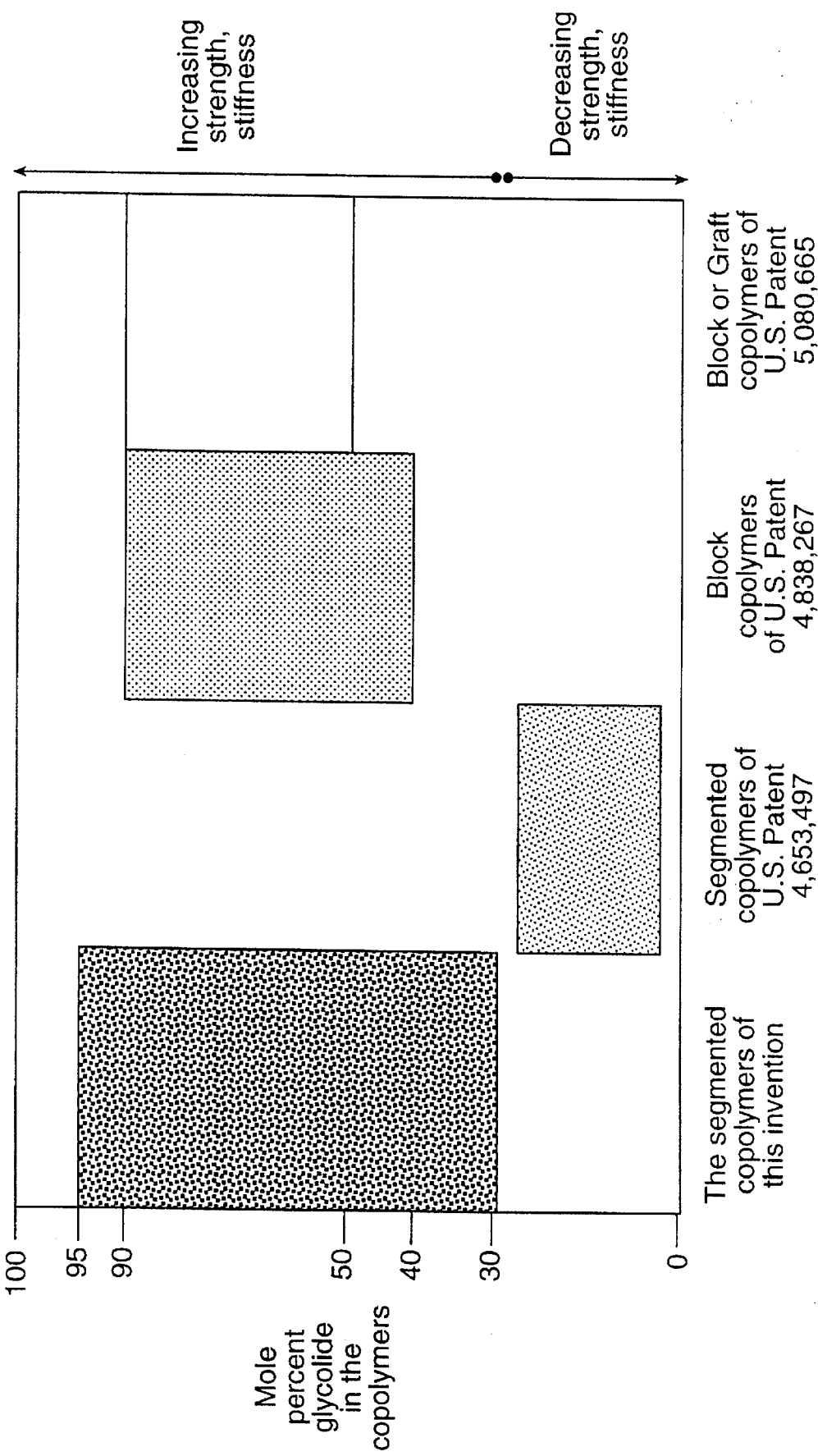
FIG. 10 shows the compositional differences between the segmented poly(glycolide-co-p-dioxanone) copolymers of the present invention and the copolymers disclosed in U.S. Pat. Nos. 4,653,497, 4,838,267 and 5,080,665.
Figure 11:
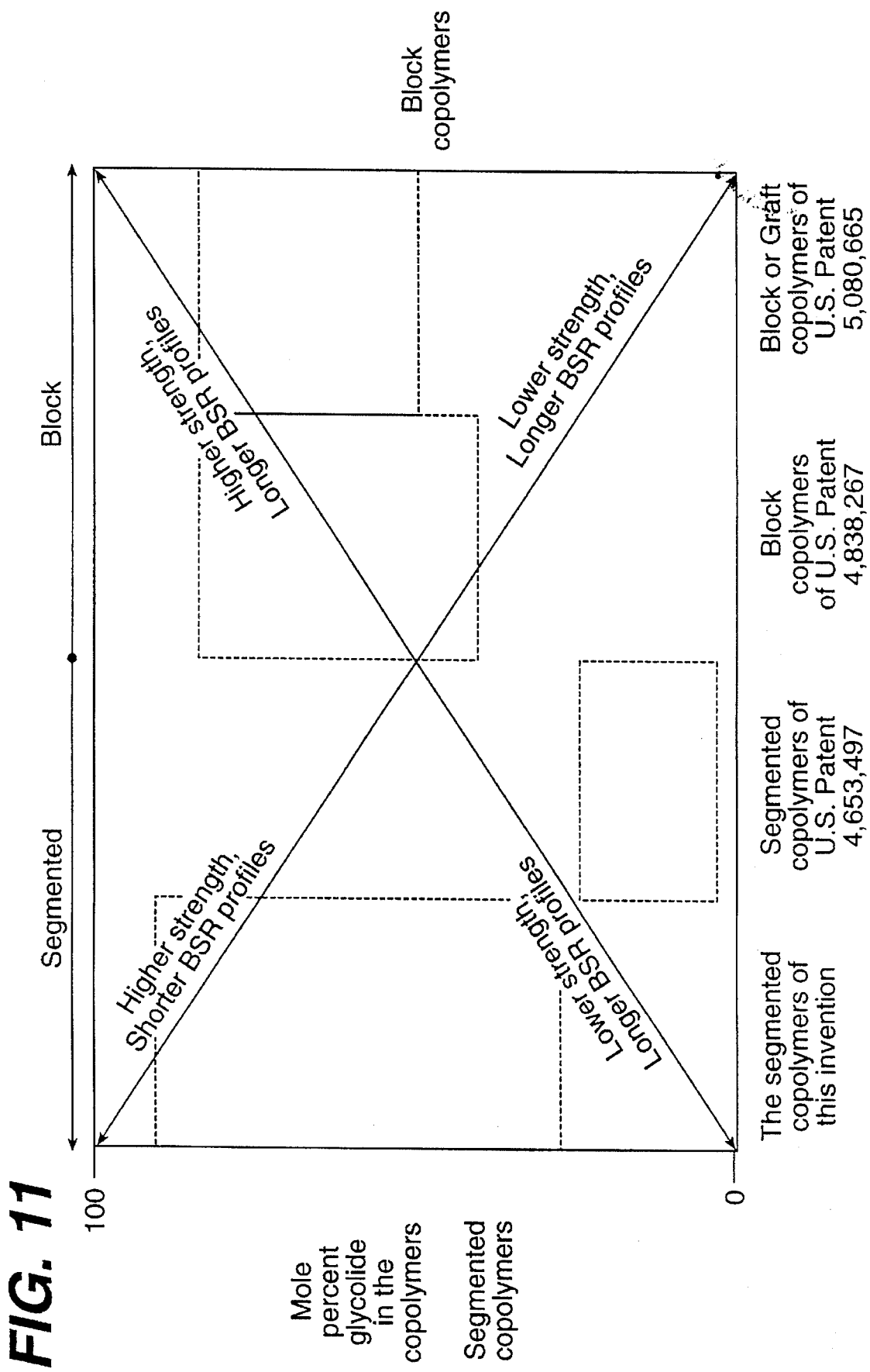
FIG. 11 displays the property differences between the segmented poly(glycolide-co-p-dioxanone) copolymers of the present invention and U.S. Pat. Nos. 4,653,497, 4,838, 267 and 5,080,665, based upon differences in composition and structure.

For biocompatible, absorbable aliphatic poly(ester)s, the sequence arrangement of repeating units in the polymer chain has a strong effect on, for example, absorption rates, BSR profiles, strength, and stiffness (FIGS. 10 and 11).

Table 1 shows the dramatic changes in physical properties by comparing the glycolide-rich, segmented poly(glycolide-co-p-dioxanone) copolymers of the present invention, and examples 2 and 3 of the poly(glycolide-b-p-dioxanone) block copolymers of U.S Pat. No. 4,838,267.

For example, it can clearly be seen in Table 1 that the block copolymers (columns 3 and 5 of Table 1) have lower tensile fiber properties than the segmented copolymers (columns 2 and 4 of Table 1). Furthermore, the block copolymers have poor conversions.

TABLE 1

| Properties of Poly(glycolide-co-p-dioxanone) segmented Copolymers and Poly(glycolide-b-p-dioxanone) Block Copolymers | | | | |
|---|---|---|---|---|
| Properties | Segmented Copolymers PGA-PDO Example 1* | Block copolymer PGA/PDO Example 2** | Segmented Copolymer PGA/PDO Example 2* | Block Copolymer PGA/PDO Example 3** |
| Initial Composition (moles) | 80/20 | 77.87/22.13 | 70/30 | 67.24/32.76 |
| Initial Composition (weight) | 81.98/18.02 | 80/20 | 77.62/27.38 | 70/30 |
| Fiber Diameter (mils) | 6.7 | 6.7 | 6.5 | 6.3 |
| Fiber Tensile Strength (psi) | 136000 | 47200 | 78000 | 57700 |
| Fiber Knot Tensile Strength (psi) | 111000 | 37000 | 69000 | 52600 |
| Fiber Elongation (%) | 12.6 | 40 | 22.7 | 52.6 |
| Fiber Young's Modulus (kpsi) | 2428 | 627 | 2007 | 551 |
| Polymerization Conversion (%) | 97 | 89 | 96 | 76 |
| Tensile Strength-Inj. molded (psi) | 11700 | | 8600 | |

**Block Copolymers are Examples 2 and 3 from U.S. Pat. No. 4,838,267
*Segmented Copolymers are Examples 1 and 2 from the present invention The 60:40 (mol/mol) poly(glycolide-co-p-dioxanone) segmented copolymer was removed from the bath, cooled to room temperature under a stream of nitrogen, isolated and ground. The copolymer conversion was about 95.7%. The inherent viscosity was 1.87 dL/g as measured in a 0.1 g/dL HFIP solution at 25° C.

As discussed above, U.S. Pat. Nos. 4,838,267, and 5,080, 665 describe poly(glycolide-co-p-dioxanone) block or graft copolymers. U.S. Pat. No. 4,653,497 describes poly(p-dioxanone)-rich, segmented poly(p-dioxanone-co-glycolide) copolymers.

The present invention describes glycolide-rich, segmented poly(glycolide-co-p-dioxanone) copolymers.

As shown in FIGS. 1, 2, 3 and 4, block copolymers are copolymers where long blocks of repeating units of each of The lower fiber properties and poor conversions of the block copolymers are caused by the sequence or arrangement of repeating units within the copolymers. That is, in the block copolymers, the polymers are composed of long sequences of both homopolymers, with some blocks of poly(p-dioxanone) on the ends of the chain (FIGS. 2 and 4). In contrast, the segmented copolymers, due to their more random sequence of repeating units, are composed mostly of glycolide end blocks (FIG. 8). Consequently, the glycolide end blocks lead to improved stability during polymerization, with less loss of p-dioxanone monomer, since it is not possible for the p-dioxanone segments to depolymerize at the end of the chain as can be found for the block copolymers. Hence, the segmented copolymers have higher conversions (i.e., less than 5 wt. % unreacted monomers, 95% or greater conversions), and better physical properties, especially fiber tensile properties. In addition, the higher conversions, and consequently, good thermal stability, found for the segmented copolymers, allows these materials to be injection molded with good tensile properties (Table 1).

In addition, the present invention requires only a single reactor process for polymerization, where the p-dioxanone monomer is polymerized to approximately 75% conversion, followed by reaction with glycolide to from copolymers with short segments of poly(p-dioxanone), poly(p-dioxanone-co-glycolide), and poly(glycolide) end blocks. In contrast, the block copolymers of U.S. Pat. No. 4,838,267, require a two-step, two reactor process, where the p-dioxanone is polymerized and then further processed by isolating, grinding, and drying to remove unreacted p-dioxanone monomer. Then, the poly(p-dioxanone) is reacted with glycolide to form block copolymers with long sequences of poly(p-dioxanone) and poly(glycolide), with some poly(p-dioxanone) end blocks.

Hence, the process of the present invention leads to the copolymers having end blocks of glycolide which prevents depolymerization and yields high conversions and excellent physical properties. Thus, the segmented copolymers of the present invention have a more elegant, simple, single reactor polymerization process than those of the block copolymers. This not only leads to advantageous properties, but is vital for large scale manufacturing development, being more cost effective and less time consuming.

Furthermore, the physical characteristics of the segmented copolymers of the present invention should allow for a variety of needs to be met for a wide range of medical devices. For example, there is a great need for absorbable polymers in plastic surgery wound closure, where high initial strength but very short BSR profiles are required. Currently, Vicryl® or Dexon® sutures are used (Table 2). Dexon® is a trademark for sutures made from braided poylcolide.

mers of the present invention, which produces improved tensile properties and fast absorption rates.

The differences in properties between the copolymers of the present invention and U.S. Pat. Nos. 4,653,497, 4,838, 267 and 5,080,665, due to differences in the structure and composition, are clearly indicated in FIG. 11. That is, surprisingly we have discovered that by moving towards compositions rich in glycolide where the copolymer structure is composed of short segments (i.e., segmented copolymer), and away from blocky structures, it is possible to obtain polymers with both high strength and short BSR profiles. That is, the block copolymer compositions yield high strength and longer BSR profiles or lower strength and longer BSR profiles. In addition, segmented copolymers, rich in p-dioxanone, yield polymers with lower strength and longer BSR profiles.

This surprising behavior is also clearly indicated in FIG. 9, which shows that the copolymers of poly(glycolide-co-p-dioxanone) of this invention have higher strength than either of the homopolymers of poly(glycolide) (i.e., Dexon®) or poly(p-dioxanone), but much shorter BSR profiles than even Vicryl®, Dexon®, poly(p-dioxanone) or the segmented p-dioxanone-rich, poly(p-dioxanone-co-glycolide) copolymers of U.S. Pat. No. 4,653,497. That is, the segmented copolymers of this invention lose all strength in less than 10 days, whereas the glycolide and p-dioxanone homopolymers and the copolymers of U.S. Pat. No. 4,653, 497 maintain strength for 3 weeks or longer.

That is, it is unexpected, based upon composition, to obtain a copolymer of poly(glycolide-co-p-dioxanone) which has the tensile strength of either of the homopolymers of poly(p-dioxanone) or poly(glycolide), but a much shorter BSR profile than either homopolymer.

Therefore, it can be seen that glycolide-rich, poly(glycolide-co-p-dioxanone) segmented copolymers of the present invention possess a surprising and unexpected unique combination of high strength and stiffness, and very

TABLE 2

Straight Tensile Strength of fibers as a function of days in-vitro DEXON (polyglycolide) VICRYL [poly(glycolide-co-lactide]) and Segmented Poly(glycolide-co-p-dioxanone) Copolymers

| Copolymer | Mole % PGA/PLA | Straight Tensile Strength (psi) | | | | | |
|---|---|---|---|---|---|---|---|
| | | Zero-day | Four-day | 7-day | 14-day | 21-day | 28-day |
| VICRYL* | 90/10 | 117000 | N/A | 95000 | 72000 | 43000 | 0 |
| DEXON* | 100/0 | 118000 | N/A | 96000 | 85000 | 44000 | 0 |
| | Weight % PGA/PDO | | | | | | |
| Example 1** | 80/20 | 136000 | 62000 | 0 | | | |
| Example 2** | 70/30 | 80000 | 36000 | 0 | | | |

*SIZE 4.0, BRAIDED
**SIZE 5.0, MONOFILAMENT

However, as shown in FIG. 9, Vicryl® has a very long BSR profile. Consequently, this can lead to tissue scaring, an event which plastic surgeons want to avoid. The segmented glycolide-rich, poly(glycolide-co-p-dioxanone) copolymers of the present invention also have high zero-day fiber tensile properties. This would also allow the surgeon to suture the wounds securely. However, because of their very fast absorption rates and very short BSR profiles, less scarring will occur (Table 2, FIG. 9) than found with currently marketed, longer BSR sutures like Vicryl® and Dexon®. This behavior is caused by the unique structure of short poly(glycolide) end blocks found in the segmented copolymers of the present invention are useful in numerous applications requiring absorbable polymers which have high strength and stiffness and short BSR profiles. They are particularly useful, for example, in plastic surgical applications where the surgeon needs to secure the wound, but requires fast absorption to prevent tissue scaring.

Although this invention has been shown and described with respect to detailed embodiments thereof, it will understood by those skilled in the art that various changes in form and detail thereof may be made without departing from the spirit and scope of the claimed invention.

We claim:

1. An absorbable, biocompatible segmented copolymer comprising:
   a major component comprising about 30 mole percent to about 95 mole percent of repeating units of glycolide; and,
   a minor component comprising about 70 mole percent to about 5 mole percent of repeating units of p-dioxanone, wherein the polymer bas a weight average molecular weight of about 10,000 grams to about 300,000 grams per mole and an inherent viscosity of about 0.5 to about 4.0 deciliters per gram.

2. The segmented copolymer of claim 1 wherein the copolymer has a molecular weight such that the inherent viscosity is from about 0.6 dL/g to about 3.0 dL/g as measured in HFIP at 25° C. at a concentration of 0.1 g/dL.

3. The segmented copolymer of claim 1 wherein the major component comprises about 30 mole percent to about 90 mole percent of repeating units of glycolide, and wherein the minor component comprises about 70 mole percent to about 10 mole percent of repeating units of p-dioxanone.

4. The segmented copolymer of claim 3 wherein the copolymer has a molecular weight such that the inherent viscosity is from about 0.6 dL/g to about 3.0 dL/g as measured in HFIP at 25° C. at a concentration of 0.1 g/dL.

5. The segmented copolymer of claim 1 wherein the repeating units of glycolide comprise about 30 mole percent to about 50 mole percent of the copolymer, and wherein the repeating units of p-dioxanone comprise about 50 mole percent to about 70 mole percent of the copolymer.

6. The segmented copolymer of claim 5 wherein the copolymer has a molecular weight such that the inherent viscosity is from about 0.6 dL/g to about 3.0 dL/g as measured in HFIP at 25° C. at a concentration of 0.1 g/dL.

7. An absorbable device for use in medical applications, the medical device comprising a segmented copolymer, said copolymer comprising:
   a major component comprising about 30 mole percent to about 95 mole percent of repeating units of glycolide; and,
   a minor component comprising about 70 mole percent to about 5 mole percent of repeating units of p-dioxanone, wherein the polymer has a weight average molecular weight of about 20,000 grams to about 300,000 grams per mole and an inherent viscosity of about 0.5 to about 4 0 deciliters per gram.

8. An absorbable device for use in medical applications, the medical device comprising a segmented copolymer, said copolymer comprising:
   a major component comprising about 30 mole percent to about 90 mole percent of repeating units of glycolide, and,
   a minor component comprising about 70 mole percent to about 10 mole percent of repeating units of p-dioxanone, wherein the polymer has a weight average molecular weight of about 20,000 grams to about 300,000 grams per mole and an inherent viscosity of about 0.5 to about 4.0 deciliters per gram.

9. An absorbable device for use in medical applications, the medical device comprising a segmented copolymer, said copolymer comprising:
   about 30 mole percent to about 50 mole percent of repeating units of glycolide; and,
   about 70 mole percent to about 50 mole percent of repeating units of p-dioxanone, wherein the polymer has a weight average molecular weight of about 20,000 grams to about 300,000 grams per mole and an inherent viscosity of about 0.5 to about 4.0 deciliters per gram.

10. A process for producing a segmented copolymer of p-dioxanone and glycolide, said process comprising heating a mixture of p-dioxanone monomer, p-dioxanone homopolymer, and glycolide monomer, to a sufficient temperature, said temperature ranging between about 100° C. and about 220° C., for a period of time to effectively produce a segmented copolymer comprising a major component comprising about 30 mole percent to about 95 mole percent of repeating units of glycolide and a minor component comprising about 70 mole percent to about 5 mole percent of repeating units of p-dioxanone.

11. A process for producing a segmented copolymer comprising the steps of:
   a) polymerizing p-dioxanone in the presence of a catalytically effective amount of catalyst and an initiator at a sufficient temperature of about 100° C. and about 130° C. and for a sufficient period of time to yield a first mixture of p-dioxanone monomer and p-dioxanone homopolymer; and
   b) adding glycolide to the first mixture to form a second mixture; and,
   c) polymerizing the second mixture at a sufficient temperature of about 180° C. to about 220° C. and for a sufficient amount of time to form a segmented copolymer comprising a major component comprising about 30 mole percent to about 95 mole percent of repeating units of glycolide and a minor component comprising about 70 mole percent to about 5 mole percent of repeating units of p-dioxanone.

12. The process of claim 11 for producing a segmented copolymer wherein the temperature for the initial polymerization is about 100° C. to about 130° C. and the time is about 5 to about 6 hours and the temperature for the second polymerization is about 180° C. to about 220° C., and the time is about 1 hour to about 4 hours.

13. The process of claim 12 wherein the amount of catalyst utilized is from about 10,000/1 to about 100,000/1, based on the molar ratio of monomer to catalyst, and wherein the catalyst is preferably tin based.

14. The process of claim 13 wherein the catalyst is stannous octoate.

15. The process of claim 12 wherein the amount of catalyst used comprises from about 100/1 to about 5,000/1, based on the molar ratio of monomer to initiator, and wherein the initiator is selected from the group consisting of alkanol, glycol, hydroxyacid, amine, and combinations thereof.

16. The process of claim 12 wherein the lactone monomer added in step (b) is glycolide and the temperature of the polymerization of the second mixture is about 180° C. to about 220° C.

17. The process of claim 16 wherein the segmented copolymer has a molecular weight such that the inherent viscosity is about 0.6 dL/g to about 3.0 dL/g as measured in HFIP at 25° C. at a concentration of 0.1 g/dL.

18. The process of claim 11 wherein the segmented copolymer comprises:
   a major component comprising about 30 mole percent to about 90 mole percent of repeating units of glycolide and,
   a minor component comprising about 70 mole percent to about 10 mole percent of repeating units of p-dioxanone, wherein the polymer has a weight average molecular weight of about 10,000 grams to about 300,000 grams per mole and an inherent viscosity of about 0.5 to about 4.0 deciliters per gram.

19. The process of claim 11 wherein the segmented copolymer comprises:
   about 30 mole percent to about 50 mole percent of repeating units of glycolide and, about 70 mole percent to about 50 mole percent of repeating units of p-dioxanone.

20. A process for manufacturing an absorbable, biocompatible segmented copolymer comprising a major component comprising about 30 mole percent to about 95 mole percent of repeating units of glycolide; and, a minor component comprising about 70 mole percent to about 5 mole percent of repeating units of p-dioxanone, wherein the polymer has a weight average molecular weight of about 10,000 grams to about 300,000 grams per mole and an inherent viscosity of about 0.5 to about 4.0 deciliters per gram, wherein said segmented copolymer comprises the product of the process comprising the steps of:

a) polymerizing p-dioxanone in the presence of a catalytically effective amount of catalyst and an initiator at a sufficient temperature of about 100° C. to about 130° C. and for a sufficient period of time to yield a first mixture of p-dioxanone monomer and p-dioxanone homopolymer; and b) adding glycolide to the first mixture to form a second mixture; and, c) polymerizing the second mixture at a sufficient temperature of about 180° C. to about 220° C. and for a sufficient amount of time.

* * * * *

UNITED STATES PATENT AND TRADEMARK OFFICE
CERTIFICATE OF CORRECTION

PATENT NO.　: 　5,633,343

DATED　　　: 　May 27, 1997

INVENTOR(S) : 　Rao S. Bezwada, Kevin Cooper, Dennis D. Jamiolkowski, Hugh D. Newman, Jr.

It is certified that error appears in the above-identified patent and that said Letters Patent is hereby corrected as shown below:

Column 14, line 6  -  "and" should be "to"

Column 14, line 15 -  "and" should be "to"

Signed and Sealed this

Eighteenth Day of November 1997

Attest:

BRUCE LEHMAN

Attesting Officer　　　Commissioner of Patents and Trademarks